United States Patent [19]

Lutomski

[11] Patent Number: 4,908,357
[45] Date of Patent: * Mar. 13, 1990

[54] PHOTOACTIVE AZOLE PESTICIDES

[75] Inventor: Kathryn A. Lutomski, Hightstown, N.J.

[73] Assignee: FMC Corporation, Philadelphia, Pa.

[ * ] Notice: The portion of the term of this patent subsequent to Dec. 13, 2005 has been disclaimed.

[21] Appl. No.: 247,974

[22] Filed: Sep. 22, 1988

Related U.S. Application Data

[63] Continuation-in-part of Ser. No. 34,259, Apr. 2, 1987, Pat. No. 4,791,124, which is a continuation-in-part of Ser. No. 908,754, Sep. 17, 1986, abandoned, which is a continuation-in-part of Ser. No. 857,883, Apr. 30, 1986, abandoned.

[51] Int. Cl.$^4$ .................... A01N 43/78; A01N 57/24; C07D 417/04; C07F 9/65
[52] U.S. Cl. ..................... 514/92; 514/365; 548/119; 548/203; 548/204; 548/205
[58] Field of Search ............... 548/203, 204, 205, 119; 514/365, 92

[56] References Cited

U.S. PATENT DOCUMENTS 4,791,124 12/1988 Lutomski et al. .................. 514/365

Primary Examiner—Richard L. Raymond
Attorney, Agent, or Firm—Robert L. Andersen; H. Robinson Ertelt

[57] ABSTRACT

Thiazole compounds of the following structural formula are photodynamic insecticides and acaricides, as well as nematicides:

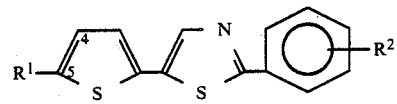

4 Claims, No Drawings

PHOTOACTIVE AZOLE PESTICIDES

This application is a continuation-in-part of application Ser. No. 034,259, filed Apr. 2, 1987, now U.S. Pat. No 4,791,124, a continuation-in-part of Ser. No. 908,754, filed 09/17/86 now abandoned, in turn a continuation-in-part of Ser. No. 857,883, filed on 4/30/86 abandoned.

This invention is in the field of heterocyclic organic chemical compounds which contain an azole nucleus. More particularly, the invention includes certain thiazole compounds per se, agricultural compositions containing the novel compounds, and the method of using a broad class of such compounds to control agricultural pests such as insects, acarids and nematodes.

There is increasing scientific evidence that toxic mechanisms initiated by light play an important role in natural control of certain pest populations. In the last few years the concept of using photoactive agents as insecticides has been advanced. Such photosensitizers typically display insecticidal activity by catalyzing the electronic triplet to singlet conversion of molecular oxygen. The excited singlet oxygen behaves as an oxidizing agent, destroying the insect tissues which it contacts, hence killing the insect.

According to the present invention, thiazole compounds of the following structural formula are photodynamic insecticides and acaricides, as well as nematicides:

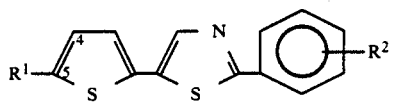

in which:

(a) $R^1$ is lower alkoxycarbonyl, lower haloalkyl, lower alkylcarbonyl, lower haloalkoxycarbonyl, phenoxycarbonyl in which the phenyl ring is unsubstituted or is substituted with at least one substituent selected from the group consisting of lower alkyl, halogen and trifluoromethyl, [1,1-biphenyl]-methyloxycarbonyl, phenylthio, lower haloalkylsulfonyl, phenylsulfonyl, nitro, cyano, a group of the formula $-C(X)NR^3R^4$ in which $R^3$ and $R^4$ are selected from the group consisting of hydrogen and lower alkyl and X is selected from oxygen and sulfur, a group of the formula $-P(X)(R^5)_2$ in which $R^5$ is selected from the group consisting of lower alkoxy and lower alkylthio, or a group of the formula $-C\equiv C-R^6$ in which $R^6$ is selected from the group consisting of lower alkyl, lower haloalkyl, phenyl and phenyl substituted with lower alkyl or halogen; and $R^2$ comprises at least one substituent selected from lower haloalkyl, lower haloalkylthio, phenylthio, nitro, cyano, lower alkylcarbonyl, lower alkoxycarbonyl, and di(lower)alkoxyphosponyl;

(b) $R^1$ is halogen or lower alkyl and $R^2$ is as defined in (a) above but is other than haloalkyl;

(c) $R^1$ is $-CH=CH-CH=CH-$ bridging positions 4 and 5 of the thienyl ring and $R^2$ is selected from hydrogen, lower alkyl, one to three halogen atoms, lower haloalkyl, or lower haloalkoxy; or (d) $R^1$ is as defined in (a) above but is other than alkoxycarbonyl and $R^2$ comprises at least one substituent selected from halogen, lower alkyl, lower haloalkoxy, and a group of the formula $-O-CF_2-O-$ bridging adjacent carbon atoms of the phenyl ring.

The terms "halo" or "halogen" when employed herein mean fluorine, chlorine or bromine. The term "lower" modifying "alkyl," "alkoxy," and the like means a straight or branched hydrocarbon chain of 1–6, preferably 1–4, carbon atoms; "halo," etc. coupled with another term means one or more hydrogen atoms has been replaced by a halogen atom, respectively.

The present invention is more specifically exemplified by the compounds set forth in Table 1, below:

TABLE 1

| Cmpd No. | $R^1$ | $R^2$ |
|---|---|---|
| 1 | $CO_2C_2H_5$ | $CF_3$ |
| 2 | $CF_3$ | $CF_3$ |
| 3 | $COCH_3$ | $CF_3$ |
| 4 | $COCF_3$ | $CF_3$ |
| 5 | $CO_2Ph$ | $CF_3$ |
| 6 | $CO_2Ph$, 4-$CH_3$ | $CF_3$ |
| 7 | $CO_2Ph$, 4-Cl | $CF_3$ |
| 8 | $CO_2Ph$, 4-F | $CF_3$ |
| 9 | $CO_2CH(Ph)_2$ | $CF_3$ |
| 10 | $C(O)NH_2$ | $CF_3$ |
| 11 | $C(O)NHCH_3$ | $CF_3$ |
| 12 | $C(O)NHCH(CH_3)_2$ | $CF_3$ |
| 13 | $C(O)N(CH_3)_2$ | $CF_3$ |
| 14 | SPh | $CF_3$ |
| 15 | $SO_2CF_3$ | $CF_3$ |
| 16 | $SO_2Ph$ | $CF_3$ |
| 17 | $P(O)(OC_2H_5)_2$ | $CF_3$ |
| 18 | $P(O)(OCH_3)_2$ | $CF_3$ |
| 19 | $P(S)(OC_2H_5)_2$ | $CF_3$ |
| 20 | $P(S)(SCH_3, OCH_3)$ | $CF_3$ |
| 21 | $NO_2$ | $CF_3$ |
| 22 | $C\equiv CCH_3$ | $CF_3$ |
| 23 | $C\equiv CCF_3$ | $CF_3$ |
| 24 | $C\equiv CPh$ | $CF_3$ |
| 25 | $C\equiv CPh$, 4-$CH_3$ | $CF_3$ |
| 26 | $C\equiv CPh$, 4-F | $CF_3$ |
| 27 | CN | $CF_3$ |
| 28 | Cl | $SCF_3$ |
| 29 | Cl | SPh |
| 30 | Cl | $NO_2$ |
| 31 | Cl | CN |
| 32 | Cl | $COCH_3$ |
| 33 | Cl | $COOCH_3$ |
| 34 | Cl | $P(O)(OC_2H_5)_2$ |
| 35 | $CH_3$ | $SCF_3$ |
| 36 | $-CH=CH-CH=CH-$ | H |
| 37 | $-CH=CH-CH=CH-$ | 4-$CH_3$ |
| 38 | $-CH=CH-CH=CH-$ | 4-$CF_3$ |
| 39 | $-CH=CH-CH=CH-$ | 3,4-$Cl_2$ |
| 40 | $-CH=CH-CH=CH-$ | $OCF_3$ |
| 41 | $COCH_3$ | Cl |
| 42 | $COCH_3$ | $CH_3$ |
| 43 | $COCH_3$ | $OCF_3$ |
| 44 | $COCH_3$ | 3-$OCF_2O-4$ |

The active compounds of this invention can be prepared by elementary modification of synthesis techniques known in the art. Attention is directed, e.g., to U.S. 4,024,156, *J. Am. Chem. Soc.*, 71, 2473 (1949), *Synth. Comm.*, 14, 1 (1984), and U.S. Pat. No. 4,153,703. Preparation of thiazole compounds of this invention is illustrated by the following specific examples.

EXAMPLE 1

5-(5-ETHOXYCARBONYLTHIEN-2-YL)-2-(4-TRIFLUOROMETHYLPHENYL)THIAZOLE

Step A 2-Bromo-1-thien-2-ylethanone

To a stirred mixture of 106.0 g (0.480 mole) of copper (II) bromide in 250 ml of ethyl acetate was added a solution of 50.0 g (0.400 mole) of 2-acetylthiophene in 250 ml of chloroform. The resultant mixture was stirred at reflux for one hour. The mixture was cooled and was filtered. An additional 50.0 g (0.224 mole) of copper (II) bromide was added to the filtrate, and this mixture was heated at reflux for one hour. This mixture was filtered, and the filtrate was evaporated under reduced pressure to yield 79.6 g of 2- bromo-1-thien-2-ylethanone as an oil.

Step B
1-(2-Oxo-2-thien-2-ylethyl)-3,5,7-triaza-1-azoniatricyclo[3,3,1,1$^{3,7}$]decane bromide To a stirred mixture of 58.0 g (0.410 mole) of hexamethylenetetramine in 900 ml of chloroform was added 77.0 g (0.380 mole) of 2-bromo-1-thien-2-ylethanone. The mixture was stirred at room temperature for approximately 18 hours. A precipitate formed and was collected by filtration. The filter cake was washed with methylene chloride and was dried to yield 122.4 g of 1-(2-oxo-2-thien-2-ylethyl)-3,5,7-triaza-1-azoniatricyclo[3,3,1,1$^{3,7}$]decane bromide.

Step C 2-Amino-1-thien-2-ylethanone hydrochloride

A mixture of 120.0 g (0.340 mole) of 1-(2-oxo-2-thien-2-ylethyl)-3,5,7-triaza-1-azoniatricyclo[3,3,1,1$^{3,7}$]decane bromide and concentrated hydrochloric acid (120 ml) in ethanol (600 ml) was stirred at room temperature for approximately 18 hours. A precipitate formed and was collected by filtration. The filter cake was dried to yield 109 g of a solid. Elemental analysis of this solid indicated that approximately 45% of the 109 g was 2-amino-1-thien-2-ylethanone hydrochloride, the remainder being chloride and bromide salts of contaminants.

Step D
N-[2-(Thien-2-yl)-2-oxoethyl]-4-trifluoromethylbenzamide

To a stirred suspension of 2-amino-1-thien-2-ylethanone hydrochloride (5.68 g of the product from Step C) and 6.66 g (0.0320 mole) of 4-trifluoromethylbenzoyl chloride in 150 ml of methylene chloride was added dropwise 32 ml of a 2 N solution of sodium hydroxide. After complete addition, the mixture was stirred at room temperature for approximately 18 hours. The reaction mixture contained a precipitate which was collected by filtration. This solid (4.8 g) was saved for further purification. The filtrate was washed with 100 ml of an aqueous, 10% hydrochloric acid solution and 100 ml of an aqueous, saturated sodium chloride solution. The washed organic phase was dried over anhydrous sodium sulfate and was filtered. This filtrate was evaporated under reduced pressure leaving a solid (4.5 g). The isolated solids (4.8 g and 4.5 g) were combined and purified by recrystallization from ethanol to yield 6.0 g of a solid. Analysis of this solid by nmr spectroscopy indicated that approximately 50% of the 6.0 g was N-[2-(thien-2-yl)-2-oxoethyl]-4-trifluoromethylbenzamide.

Step E
2-(4-Trifluoromethylphenyl)-5-thien-2-ylthiazole

Under a dry nitrogen atmosphere N-[2-(thien-2-yl)-2-oxoethyl]-4-trifluoromethylbenzamide (5.6 g of the solid from Step D) was added to a stirred suspension of [2,4-bis-(4-methoxyphenyl)-1,3-dithia-2,4-diphosphetane-2,4-disulfide (Lawesson's reagent) (3.6 g, 0.0090 mole) in 150 ml of toluene. The resultant mixture was heated at reflux for four hours, then was allowed to cool to room temperature, and was stirred for approximately 18 hours. The mixture was heated at reflux for three hours and then was cooled. The solvent was removed from the mixture by evaporation under reduced pressure, leaving a residue. This residue was purified by column chromatography on silica gel, eluting with methylene chloride:n-hexane (3:1) to yield 2.84 g of 2-(4-trifluoromethylphenyl)-5-thien-2-ylthiazole, as a solid, mp 153.5°–155° C.

The nmr spectrum was consistent with the proposed structure.

Step F
5-(5-Ethoxycarbonylthien-2-yl)-2-(4-trifluoromethylphenyl)thiazole

Under a dry nitrogen atmosphere, 1.6 ml of a 2.5 M solution of n-butyllithium in n-hexane was added dropwise to a stirred, cold (−78° C.) solution of 1.0 g (0.0032 mole) of 2-(4-trifluoromethylphenyl)-5-thien-2-ylthiazole in 15 ml of tetrahydrofuran. This mixture was stirred at −78° C. for two hours and then was added to a stirred, cold (−78° C.) solution of 0.70 g (0.0064 mole) of ethylchloroformate in 20 ml of tetrahydrofuran. After complete addition the mixture was allowed to warm to room temperature and was stirred for approximately 18 hours. The mixture was diluted with 100 ml of diethyl ether and was washed in succession with an aqueous, saturated ammonium chloride solution, water, and an aqueous, saturated sodium chloride solution. The organic phase was dried over anhydrous magnesium sulfate and was filtered. The filtrate was evaporated under reduced pressure, leaving a solid. This solid was purified by column chromatography on silica gel, eluting with methylene chloride:n-hexane (60:40) to yield 0.56 g of 5-(5-ethoxycarbonylthien-2-yl)-2-(4-trifluoromethylphenyl)thiazole as a solid, compound 1 of Table 1.

The nmr and ir spectra were consistent with the proposed structure

EXAMPLE 2
2-(4-Trifluoromethylthiophenyl)-5-(5-methylthien-2-yl)thiazole

Step A N-[2-(5-methyl thien-2-yl)-2-oxoethyl]-4-trifluoromethylthiobenzamide To a stirred mixture of 8.13 g (0.46 mole) of 2-amino-1-(5-methylthien-2-yl)ethanone hydrochloride (prepared in a manner similar to Steps A-C of Example 1 from 2-acetyl-5- methylthiophene) in 250 ml of methylene chloride was added a solution of 11.9 g (0.0460 mole) of 4-trifluoromethylthiobenzoyl chloride in 50 ml of methylene chloride. The resulting suspension was cooled to −20° C., and 25 ml of an aqueous 4N sodium hydroxide solution was added dropwise. The reaction mixture was allowed to warm to room temperature and stir for approximately 18 hours. The reaction mixture was transferred to a separatory funnel and was washed in succession with an aqueous, 10% sodium hydroxide solution, an aqueous, saturated sodium chloride solution, an aqueous, 10% hydrochloric acid solution, and an aqueous, saturated sodium carbonate solution. The washed organic phase was dried over anhydrous magnesium sulfate and was filtered. The filtrate was evaporated under reduced pressure, leaving a solid residue. This residue was triturated with diethyl either, filtered, and was dried to yield 10.9 g of N-[2-(5-methylthien-2- yl)-2-oxoethyl]-4-trifluoromethylthiophenylbenzamide, mp 160°–164° C.

The nmr spectrum was consistent with the proposed structure.

Step B
2-(4-Trifluoromethylthiophenyl)-5-(5-methylthien-2-yl)thiazole

In a manner similar to Step E of Example 1, the reaction of 6.24 g (0.0174 mole) of N-[2-(5-methylthien-2-yl)-2-oxoethyl]-4-trifluoromethylthiobenzamie and 3.60 g (0.00891 mole) of Lawesson's reagent in 150 ml of toluene yielded 4.47 g of 2-(4-trifluoromethylthiophenyl)-5-(5-methylthien-2-yl)thiazole as a solid, mp 131°–133° C., compound 35 of Table 1.

The nmr spectrum was consistent with the proposed structure.

EXAMPLE 3

2-(4-TRIFLUOROMETHOXYPHENYL)-5-THIANAPHTHALENE-2-YLTHIAZOLE

Step A 2-Acetylthianaphthalene

Under a dry nitrogen atmosphere, 7.18 g (0.0914 mole) of acetyl chloride was added to a cold (5° C.), stirred mixture of 11.9 g (0.0893 mole) of aluminum chloride in 100 ml of carbon tetrachloride. To this mixture was added a solution of 10.6 g (0.079 mole) of thianaphthalene in 25 ml of carbon tetrachloride. The reaction mixture was allowed to warm to room temperature and was stirred for two hours. The mixture was heated at reflux for 45 minutes and was cooled. The resultant mixture was poured into ice water, and 100 ml of concentrated hydrochloric acid was added. This mixture was stirred until the ice melted. The organic phase was removed and saved. The aqueous phase was extracted with methylene chloride. The organic phases were combined and dried over anhydrous sodium sulfate. This mixture was filtered, and the filtrate was treated with silica gel and decolorizing charcoal. The resulting mixture was filtered through a pad of silica gel. The filtrate was evaporated under reduced pressure to yield 11.3 g of 2-acetylthianaphthalene as an oil.

The nmr spectrum was consistent with the proposed structure.

Step B 2-Bromo-1-thianaphthalene-2-ylethanone

To a stirred solution of 7.47 g (0.0424 mole) of 2-acetylthianaphthalene in 80 ml of methylene chloride and 40 ml of ethyl acetate was added 9.53 g (0.0426 mole) of copper (II) bromide. The resultant mixture was heated at reflux for two hours. The reaction mixture was filtered, and an additional 9.63 g (0.0431 mole) of copper (II) bromide was added. This mixture was heated at reflux for two hours. The above process was repeated, the mixture was filtered, 9.0 g (0.0403 mole) of copper (II) bromide was added, and the mixture was heated at reflux for two hours. The reaction mixture was filtered, and the filtrate was treated with decolorizing charcoal. This mixture was filtered through a pad of silica gel. The filtrate was evaporated under reduced pressure, leaving a solid residue. This residue was triturated in diethyl ether and pentane to yield 8.91 g of 2-bromo-1-thianaphthalene-2-ylethanone.

The nmr spectrum was consistent with the proposed structure.

This reaction was repeated to produce an additional 2.0 g of 2-bromo-1-thianaphthalene-2-ylethanone.

Step C
1-(2-Oxo-2-thianaphthalene-2-ylethyl)-3,5,7-triaza-1-azoniatricyclo[3,3,1,1$^{3,7}$]-decane bromide In a manner similar to Step B of Example 1, the reaction of 10.4 g (0.0410 mole) of 2-bromo-1-thianaphthalene-2-ylethanone with 6.69 g (0.0478 mole) of hexamethylenetetramine in 250 ml of methylene chloride yielded 10.5 g of 1-(2-oxo-2-thianaphthalene-2-ylethyl)-3,5,7-triaza-1-azoniatricyclo[3,3,1,1$^{3,7}$]decane bromide.

Step D 2-Amino-1-thianaphthalene-2-ylethanne hydrochloride

In a manner similar to Step C of Example 1, the reaction of 10.3 g (0.0261 mole) of 1-(2-oxo-2-thianaphthalene-2-ylethyl)-3,5,7-triaza-1-azoniatricyclo[3,3,1,1$^{3,7}$]-decane bromide with 11.5 ml of concentrated hydrochloric acid in 250 ml of ethanol yielded 10.8 g of a solid. Analysis of this solid by nmr spectroscopy indicated that approximately 30% of the 10.8 g was 2-amino-1-thianaphthalene-2-ylethanone hydrochloride, the remainder being chloride and bromide salts of contaminants.

Step E
N-[2-(Thianaphthalene-2-yl)-2-oxoethyl]-4-trifluoromethoxybenzamide

In a manner similar to Step D of Example 1, the reaction of 2-amino-1-thianaphthalene-2-ylethanone hydrochloride (3.0 g of the product from Step D) with 1.18 g (0.00527 mole) of 4-trifluoromethoxybenzoyl chloride and 2.64 ml of an aqueous, 4N sodium hydroxide solution in 40 ml of methylene chloride produced 1.1 g of N-[2-(thianaphthalene-2-yl)-2-oxoethyl]-4-trifluoromethoxybenzamide as a solid.

Step F
2-(4-Trifluoromethoxyphenyl)-5-(thianaphthalene-2-yl)thiazole

In a manner similar to Step E of Example 1, the reaction of 1.0 g (0.0026 mole) of N-[2-(thianaphthalene-2-yl)-2oxoethyl]-4-trifluoromethoxybenzamide with 0.53 g (0.0013 mole) of Lawesson's reagent in 25 ml of toluene yielded 0.45 g of 2-(4-trifluoromethoxyphenyl)-5-(thianaphthalene-2-yl)thiazole as a solid, mp 65–69, compound 40 of Table 1.

The nmr spectrum was consistent with the proposed structure.

In the normal use of the pesticidal azole compounds of the present invention, the active compounds usually will not be employed free from admixture or dilution, but ordinarily will be used in a suitable formulated composition compatible with the method of application and comprising an insecticidally, acaricidally, or nematicidally effective amount of active compound. The active compounds of this invention, like most pesticidal agents, may be blended with the agriculturally acceptable surface-active agents and carriers normally employed for facilitating the dispersion of active ingredients, recognizing the accepted fact that the formulation and mode of application of a pesticide may affect the activity of the material. The present active compounds may be applied, for example, as sprays, dusts, or granules to the area where pest control is desired, the type of application varying, of course, with the pest and the environment. Thus, the active compounds of this invention may be formulated as granules of large particle size, as powdery dusts, as wettable powders, as emulsifiable concentrates, as solutions, and the like.

Granules may comprise porous or nonporous particles, such as attapulgite clay or sand, for example, which serve as carriers for the active compounds. The granule particles are relatively large, a diameter of about 400–2500 microns typically. The particles are either impregnated with the active compound from solution or coated with the active compound, adhesive sometimes being employed. Granules generally contain 0.05–10%, preferably 0.5–5%, active ingredient as the pesticidally effective amount.

Dusts are admixtures of the active compound with finely divided solids such as talc, attapulgite clay, kieselguhr, pyrophyllite, chalk, diatomaceous earths, calcium phosphates, calcium and magnesium carbonates, sulfur, flours, and other organic and inorganic solids or nematicide. These finely divided solids have an average particle size of less than about 50 microns. A typical dust formulation useful for controlling insects, acarids, or nematodes may contain, for example, 1 part of active compound, and 99 parts of talc.

The active compounds of the present invention may be made into liquid concentrates by dissolution or emulsification in suitable liquids and into solid concentrates by admixture with talc, clays, and other known solid carriers used in the pesticide art. The concentrates are compositions containing, as a pesticidally effective amount, about 5–50% active compound and 95–50% inert material, which includes surface-active dispersing, emulsifying, and wetting agents, but even higher concentrations of active ingredient may be employed. The concentrates are diluted with water or other liquids for practical application as sprays, or with additional solid carrier for use as dusts.

A typical 25% wettable powder formulation may, for example, consist of 25.0% (wt/wt) active ingredient, and 75.0% base consisting of 2.0% sodium ligninsulfonate, 2% sodium alkylnaphthalene sulfonate and 96% attapulgite clay.

Typical carriers for solid concentrates (also called wettable powders) include fuller's earth, clays, silicas, and other highly absorbent, readily wetted inorganic diluents. A solid concentrate formulation useful for controlling insects, acarids, or nematodes may contain, for example, 1.5 parts each of sodium lignosulfonate and sodium laurylsulfate as wetting agents, 25 parts of active ingredient, and 72 parts of attapulgite clay.

Manufacturing concentrates are useful for shipping low melting products of this invention. Such concentrates are prepared by melting the low melting solid products together with one percent or more of a solvent to produce a concentrate which does not solidify on cooling to the freezing point of the pure product or below.

Useful liquid concentrates include the emulsifiable concentrates, which are homogeneous liquid or paste compositions readily dispersed in water or other liquid carriers. They may consist entirely of the active compound with a liquid or solid emulsifying agent, or they may also contain a liquid carrier such as xylene, heavy aromatic naphthas, isophorone and other relatively nonvolatile organic solvents. For application, these concentrates are dispersed in water or other liquid carriers and normally applied as sprays to areas to be treated.

A typical 50 gram per liter emulsifiable concentrate formulation may, for example, consist of 5.90% (wt/wt) of active ingredient; as emulsifiers: 1.80% of a blend of the calcium salt of dodecylbenzene sulfonate and a nonionic 6-molar ethylene oxide condensation product of nonylphenol, 2.70% of a blend of the calcium salt of dodecylbenzene sulfonate and a nonionic 30-molar ethylene oxide condensation product of nonylphenol, 1 50% of a nonionic paste of polyalkylene glycol ether; and 88.10% refined xylene solvent.

Typical surface-active wetting, dispersing, and emulsifying agents used in pesticidal formulations include, for example, the alkyl and alkylaryl sulfonates and sulfates and their sodium salts; alkylamide sulfonates, including fatty methyl taurides; alkylaryl polyether alcohols, sulfated higher alcohols, polyvinyl alcohols; polyethylene oxides; sulfonated animal and vegetable oils, sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises about 1–15% by weight of the insecticidal, acaricidal, or nematicidal composition.

Other useful formulations include simple solutions of the active ingredient in a solvent in which it is completely soluble at the desired concentration, such as acetone or other organic solvents.

An insecticidally, acaricidally, or nematicidally effective amount of active compound in an insecticidal, acaricidal, or nematicidal composition diluted for application is normally in the range of about 0.001% to about 8% by weight. Many variations of spraying and dusting compositions known in the art may be used by substituting the active compounds of this invention into compositions known or apparent in the art.

The insecticidal, acaricidal, or nematicidal compositions of this invention may be formulated with other active ingredients, including other insecticides, nematicides, acaricides, fungicides, plant growth regulators, fertilizers, etc. In using the compositions to control insects, acarids, or nematodes, it is only necessary that an insecticidally, acaricidally, or nematicidally effective amount of azole compound be applied to the locus where control is desired. Such locus may, e.g., be the pests themselves, plants upon which the pests feed, or the pest habitat. When the locus is soil, e.g., soil in which agricultural crops are or will be planted, the active compound may be applied to and optionally incorporated into the soil. For most applications, an insecticidally, acaricidally, or nematicidally effective amount will be about 50 to 750 g per hectare, preferably 150 g to 500 g per hectare.

The pesticidal activity of the active compounds whose preparation is described above was evaluated as follows:

The compounds were tested for insecticidal and acaricidal activity under near ultraviolet light (wavelength 320–400 nanometers) at an intensity of 1600–2400 microwatts/$cm^2$ using test procedures adapted to the various organisms in the test. Regardless of the organism, foliage of whole plants or foliage removed from whole plants was sprayed to runoff with a 10% acetone-0.25% octylphenoxypolyethoxyethanol-water solution containing up to 200 ppm of the test compound.

A whole pinto bean plant (*Phaseolus vulgaris*) was sprayed with chemical as described above and was allowed to dry. Leaves infested with adult twospotted spider mites (*Tetranychus urticae*) were removed from culture plants and cut into segments containing 50-75 female mites. Each segment was placed on the upper leaf surface of a treated pinto bean plant. After the mites had migrated to the under surfaces of the leaves, the leaf segments used to infest were removed. The entire plant and pot were placed in metal trays in a hood. A supply of water in the tray kept the plants turgid.

In tests utilizing cabbage looper (*Trichoplusia ni*), the pinto bean test plants were sprayed with test chemical and allowed to dry as previously described. After drying, a single leaf was removed and placed in a petri dish lined with a moistened cotton pad. The insects were added and the dish was transferred to an environmental chamber maintained at 27° C. and about 50% relative humidity. The chamber was irradiated with ultraviolet light. After approximately 18 hours, the leaves were removed from each petri dish and a piece of artificial diet was added. The petri dishes were then returned to the chamber for the remainder of the exposure period.

The test results were collected and recorded at the end of a 48 hour exposure period. These data appear in Table 2. In contrast to the results shown in Table 2, in the absence of ultraviolet irradiation, at application rates of 1000 ppm, the compounds generally failed to kill the insects and acarids.

TABLE 2

| | | | Foliar Testing | |
|---|---|---|---|---|
| | | | Species (% Kill or LC$_{50}$, ppm) | |
| FMC | Cmpd. of Ex. | Rate (ppm) | CL | TSM-S |
| 107496 | 1 | 50 | 70% | 2.0 ppm |
| 118343 | 35 | 50 | 58% | 2.1 ppm |
| 118386 | 36 | 50 | 0 | 5% |
| 118387 | 37 | 50 | 0 | 10% |
| 118388 | 38 | 50 | 25% | 16.3 ppm |
| 118389 | 39 | 50 | 0 | 19.6 ppm |
| 118390 | 40 | 50 | 20% | 7.6 ppm |

CL = Cabbage looper
TSM-S = Twospotted spider mite - phosphate susceptible

We claim:
1. A compound of the formula

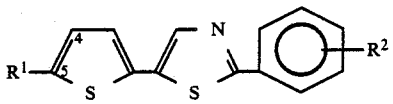

in which
(a) R$^1$ is lower alkoxycarbonyl, lower haloalkyl, lower alkylcarbonyl, lower haloalkoxycarbonyl, phenoxycarbonyl in which the phenyl ring is unsubstituted or is substituted with at least one substituent selected from the group consisting of lower alkyl, halogen and trifluoromethyl, [1,1-biphenyl]-methyloxycarbonyl, phenylthio, lower haloalkylsulfonyl, phenylsulfonyl, nitro, cyano, a group of the formula —C(X)NR$^3$R$^4$ in which R$^3$ and R$^4$ are selected from the group consisting of hydrogen and lower alkyl and X is selected from oxygen and sulfur, a group of the formula —P(X)(R$^5$)$_2$ in which R$^5$ is selected from the group consisting of lower alkoxy and lower alkylthio, or a group of the formula —C=C—R$^6$ in which R$^6$ is selected from the group consisting of lower alkyl, lower haloalkyl, phenyl and phenyl substituted with lower alkyl or halogen; and R$^2$ is at least one substituent selected from lower haloalkyl, lower haloalkylthio, phenylthio, nitro, cyano, lower alkylcarbonyl, lower alkoxycarbonyl, and di(lower)alkoxyphosphonyl;
(b) R$^1$ is halogen or lower alkyl and R$^2$ is as defined in (a) above but is other than haloalkyl;
(c) R$^1$ is —CH=CH—CH=CH— bridging positions 4 and 5 of the thienyl ring and R$^2$ is selected from hydrogen, lower alkyl, one to three halogen atoms, lower haloalkyl, or lower haloalkoxy; or
(d) R$^1$ is as defined in (a) above but is other than alkoxycarbonyl and R$^2$ comprises at least one substituent selected from halogen, lower alkyl, lower haloalkoxy, and a group of the formula —O—CF$_2$—O— bridging adjacent carbon atoms of the phenyl ring.

2. The compound of claim 1 in which R$^2$ is trifluoromethyl or trifluoromethylthio.

3. An insecticidal or acaricidal composition comprising an insecticidal or acaricidal amount of the compound of claim 1 or 2 in admixture with a compatible agriculturally acceptable adjuvant, diluent or carrier.

4. A method for controlling insects or acarids which comprises applying to the locus where control is desired an insecticidally or acaricidally effective amount of a compound of claim 1 or 2.

* * * * *